(12) United States Patent
Sugise et al.

(10) Patent No.: US 6,844,464 B2
(45) Date of Patent: Jan. 18, 2005

(54) PROCESS FOR PRODUCING ALKYL NITRITE

(75) Inventors: Ryoji Sugise, Ube (JP); Shuji Tanaka, Ube (JP); Hirofumi Ii, Ube (JP); Kazuaki Mii, Ube (JP)

(73) Assignee: Ube Industries, Ltd. (JP)

( * ) Notice: Subject to any disclaimer, the term of this patent is extended or adjusted under 35 U.S.C. 154(b) by 40 days.

(21) Appl. No.: 10/388,302

(22) Filed: Mar. 13, 2003

(65) Prior Publication Data

US 2003/0176724 A1 Sep. 18, 2003

(30) Foreign Application Priority Data

Mar. 18, 2002 (JP) ........................................ 2002-073693
Mar. 25, 2002 (JP) ........................................ 2002-082600

(51) Int. Cl.$^7$ ............................................ C07C 203/02
(52) U.S. Cl. ........................................................ 558/488
(58) Field of Search ........................................ 558/488

(56) References Cited

U.S. PATENT DOCUMENTS 2,831,882 A   4/1958  Spaeth
4,353,843 A * 10/1982  Doumaux et al. .......... 558/488
4,908,466 A *  3/1990  Nelson ........................ 558/488

FOREIGN PATENT DOCUMENTS

| EP | 0 076 217 A | 4/1983 |
| EP | 0 310 191 A | 4/1989 |
| EP | 0 911 316 A | 4/1999 |
| FR | 2 807 035 A | 10/2001 |
| JP | 6-25104 | 2/1994 |
| JP | 6-298706 | 10/1994 |
| JP | 11-189570 | 7/1999 |

OTHER PUBLICATIONS

Liquid Phase Catalytic Oxidation of Nitric Oxide with Nitric Acid, Osa et al., Chemistry Letters, 1976, pp. 1029–1032.

* cited by examiner

*Primary Examiner*—Johann Richter
*Assistant Examiner*—Ebenezer Sackey
(74) *Attorney, Agent, or Firm*—Piper Rudnick LLP

(57) ABSTRACT

An alkyl nitrite is produced with high efficiency by bringing a nitrogen monoxide gas into contact with an aqueous solution of an alkyl alcohol and nitric acid in a reactor 2, which aqueous solution may be a liquid fraction generated in an alkyl nitrite-production process in which an alkyl alcohol is reacted with nitrogen monoxide and oxygen in a reaction column 1.

8 Claims, 3 Drawing Sheets

PROCESS FOR PRODUCING ALKYL NITRITE

TECHNICAL FIELD

The present invention relates to a process for producing an alkyl nitrite from nitric acid, which may be a by-product of a process for producing an alkyl nitrite from nitrogen monoxide, oxygen and an alkyl alcohol, nitrogen monoxide, and an alkyl alcohol, with high efficiency.

The alkyl nitrite is useful as a material for producing other alkyl esters, for example, dialkyl oxalate and dialkyl carbonate, through oxidation processes.

BACKGROUND ART

As a process for producing an alkyl nitrite by reaction of an alkyl alcohol with nitrogen monoxide and oxygen, Japanese Unexamined Patent Publication No. 11-189,570 and No. 6-298,706 disclose a process in which an alkyl alcohol is fed into a top portion of a reaction column and allowed to fall from the top portion to the bottom portion through a middle portion of the reaction column; separately, nitrogen monoxide and oxygen gasses are fed separately or together into the bottom portion of the reaction column and allowed to flow upward through the reaction column and react with the falling alkyl alcohol to produce an alkyl nitrite; and the resultant gas fraction containing the alkyl nitrite is collected through an outlet located in the top portion of the reaction column.

This process is however, unsatisfactory in that nitric acid is produced as a by-product, in a relatively large amount, and thus a large amount of the nitrogen materials for the process is in advantageously consumed. Therefore, it is desirable that the nitric acid is effectively utilized to increase the efficiency of the production of the target alkyl nitrite.

Japanese Unexamined Patent Publication No. 6-25,104 discloses a process, for continuously producing dimethyl carbonate from carbon monoxide and methyl nitrite, in which nitrogen monoxide produced as a by-product is utilized to react with oxygen and methyl alcohol to regenerate methyl nitrite and in this methyl nitrite-regeneration procedure, nitric acid is utilized as a nitrogen-supply source. In this process, nitric acid is thermally decomposed to generate nitrogen oxides. However, the decomposition is carried out with an unsatisfactory efficiency and the effective decomposition temperature is very limited. In this reaction system, nitric acid and nitrogen monoxide may contact methyl alcohol. However, the inventors of the present invention found that in the reaction system for producing methyl nitrite from nitrogen monoxide, oxygen and methyl alcohol, oxygen gas fed into the reaction system causes the concentrations of oxygen and nitrogen dioxide in the reaction gas to increase, and therefore, the production of methyl nitrite from nitric acid, nitrogen monoxide and methyl alcohol with a high efficiency is very difficult.

Also, Japanese Unexamined Patent Publication No. 11-189,570 discloses a process for producing an alkyl nitrite by withdrawing a liquid fraction collected in a bottom portion of an alkyl nitrite regeneration reaction column and containing nitric acid from the reaction column, and cooling and recycling the withdrawn liquid fraction through the reaction column and a cooler. In connection with this reaction system, the inventors of the present invention found that while a contact of nitric acid and the alkyl alcohol with nitrogen monoxide occurs in the reaction system, the reaction system contains oxygen and nitrogen dioxide in increased concentrations due to the feed of oxygen into the reaction system and, therefore, the production of the alkyl nitrite from nitric acid, nitrogen monoxide and the alkyl alcohol with a high production efficiency is very difficult.

Chemistry Letters, 1029 (1976) discloses that when nitrogen dioxide is produced by a reaction of nitric acid with nitrogen monoxide as shown in reaction formula (1):

$$NO + 2HNO_3 \rightarrow 3NO_2 + H_2O \tag{1}$$

in an initial stage of the reaction (1), a reaction shown in reaction formula (2) occurs.

$$NO + HNO_3 \rightarrow NO_2 + HNO_2 \tag{2}$$

However, the reaction (2) is disadvantageous in that the equilibrium of the reaction (2) greatly deviates to the original system side, and thus, the production of nitrogen dioxide and nitrous acid in high concentration is difficult and, when the equilibrium of the reaction (2) is moved to the resultant product system side, as the solubility of nitrogen dioxide in water is relatively high and, in the reaction system, nitrogen dioxide, nitrous acid and nitric acid are equilibrates with each other, an increase in the concentration of nitrogen dioxide or in the reaction pressure, causes the production of nitric acid to increase and as a result, the production of nitrogen dioxide at a high concentration becomes difficult. Due to the above-mentioned disadvantages, the inventors of the present invention concluded that the above-mentioned process is unsatisfactory as an industrial practice for producing nitrogen dioxide and nitrous acid from nitric acid. Further, Encyclopaedia Chinrica, volume 1, 32nd Printing in Reduced Size, page 665, discloses a process for producing nitrogen monoxide by reducing a concentrated nitric acid with a bismuth, copper, led or mercury metal or iron oxide (II) or diarsenic trioxide. This process utilizes a stoichiometric reaction and thus, the reducing material comprising the above mentioned metal or oxide must be employed in a large amount. Therefore, the above-mentioned process is inadequate in industrial practice.

SUMMARY OF THE INVENTION

The present invention intends to provide a process for producing an alkyl nitrite from an alkyl alcohol, nitrogen monoxide and nitric acid which may be a by-product of a process for producing an alkyl nitrite from an alkyl alcohol, nitrogen monoxide and oxygen, with a high efficiency and with a high industrial utilizability.

The process of the present invention for producing an alkyl nitrite comprises bringing a nitrogen monoxide gas into contact with an aqueous solution of an alkyl alcohol and nitric acid, to produce an alkyl nitrite.

In the process of the present invention for producing an alkyl nitrite, the alkyl alcohol preferably has 1 to 3 carbon atoms.

In the process of the present invention for producing an alkyl nitrite, the aqueous solution preferably contains nitric acid in a concentration of 60% by mass or less.

In the process of the present invention for producing an alkyl nitrite, the aqueous solution preferably contains the alkyl alcohol in a concentration of 5 to 70% by mass.

In the process of the present invention for producing an alkyl nitrite, the contacting of the nitrogen monoxide gas with the aqueous solution of the alkyl alcohol and nitric acid is preferably carried out at a temperature of from 0° C. to 200° C., under ambient atmospheric pressure or more but not more than 20 MPa G.

In the process of the present invention for producing an alkyl nitrite, the aqueous solution of the alkyl alcohol and nitric acid optionally further contains a catalyst comprising at least one nitrate salt of Group VIII metals except for platinum group metals and of Group IB metals of the Periodic Table.

In the process of the present invention for producing an alkyl nitrite, the catalyst is preferably present in an amount, in terms of metal, of 20% by mass or less, based on the mass of the aqueous solution containing the alkyl alcohol and nitric acid.

In the process of the present invention for producing an alkyl nitrite, the nitrogen monoxide gas is preferably substantially free from nitrogen oxides produced due to the presence of molecular oxygen contained in the nitrogen monoxide gas.

In the process of the present invention for producing an alkyl nitrite, the nitrogen monoxide gas is preferably substantially free from nitrogen dioxide, dinitrogen trioxide, dinitrogen tetraoxide and molecular oxygen.

In an embodiment of the process of the present invention for producing an alkyl nitrite, (A) the aqueous solution of the alkyl alcohol and nitric acid is prepared in a reaction column by procedures such that the alkyl alcohol is fed into a top portion of the reaction column while allowing the fed alkyl alcohol to fall down through the reactor column; nitrogen monoxide and oxygen gasses are fed separately or together into a bottom portion of the reaction column while allowing the fed nitrogen monoxide and oxygen gases to flow upward through the reaction column and to react with the falling alkyl alcohol; the resultant gas fraction containing alkyl nitrite gas is delivered through a top outlet of the reaction column and the resultant liquid fraction containing the non-reacted alkyl alcohol and nitric acid dissolved in water is collected in a bottom portion of the reaction column; and the collected liquid fraction is withdrawn from the bottom portion of the reaction column and a portion of the withdrawn liquid fraction is fed into a reactor, and (B) in the reactor, a nitrogen monoxide gas is brought into contact with the fed liquid fraction, to produce an alkyl nitrite.

In the embodiment of the process of the present invention for producing an alkyl nitrite, preferably a gas fraction produced in the reactor and containing the alkyl nitrite is withdrawn from the reactor and introduced into a portion located between the bottom and middle portions of the reaction column, the introduced gas fraction is allowed to flow upward together with the gas fraction produced in the reactor column through the reactor column and to be refined with the falling alkyl alcohol, and the refined alkyl nitrite gas is delivered through the top outlet of the reaction column.

In the embodiment of the process of the present invention for producing an alkyl nitrite, preferably, the nitrogen monoxide gas for the reactor is supplied from the same source as that for the reaction column.

In the embodiment of the process of the present invention for producing an alkyl nitrite, preferably, the portion of the liquid fraction fed from the bottom of the reaction column into the reactor contains nitric acid in a concentration of 20% by mass or less and the non-reacted alkyl alcohol in a concentration of 15 to 60% by mass.

In the embodiment of the process of the present invention for producing an alkyl nitrite, preferably, another portion of the liquid fraction withdrawn from the bottom portion of the reaction column is cooled through a cooler and recycled into middle portion of the reaction column.

In the embodiment of the process of the present invention for producing an alkyl nitrite, preferably, the recycling procedures of the another portion of the liquid fraction from the bottom portion into the middle portion through the cooler is continuously carried out, while (a) the recycling rate, in terms of mass, of the another portion of the liquid fraction is controlled to 50 to 300 times the feed rate, in terms of mass, of the alkyl alcohol into the reaction column;

(b) the total of the feed rate, in terms of mole, of the alkyl alcohol into the reaction column and the recycling rate, in terms of mole, of the non-reacted alkyl alcohol contained in the recycled portion of the liquid fraction is controlled to 20 to 150 times the feed rate, in terms of mole, of whole nitrogen oxides into the reaction column, and (c) the concentration of the non-reacted alkyl alcohol in the liquid fraction collected in the bottom portion of the reaction column is controlled to 15 to 60% by mass.

BEST MODE OF CARRYING OUT THE INVENTION

Figure 1:
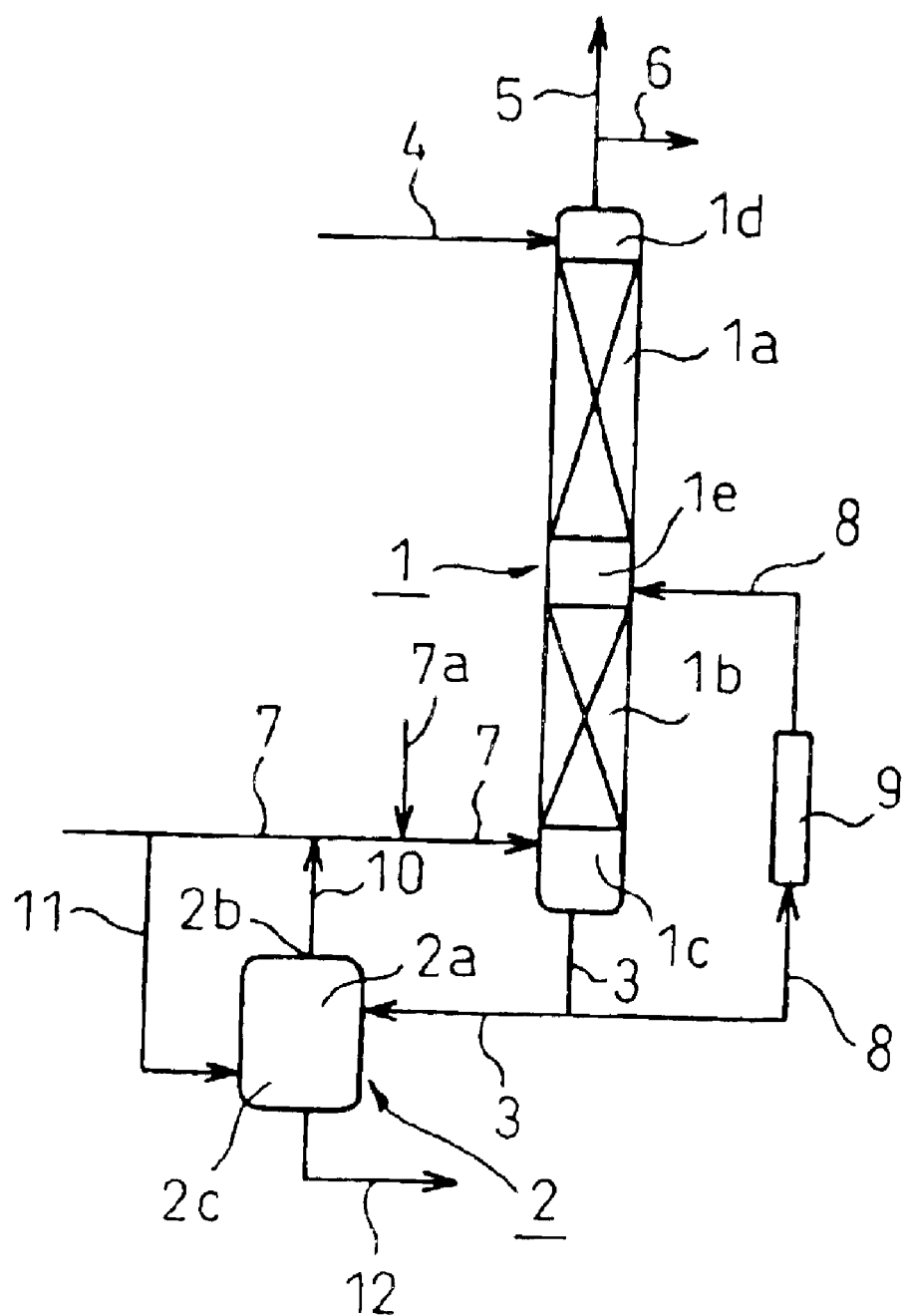
FIG. 1 is a flow sheet showing an embodiment of the process of the present invention for producing an alkyl nitrite.

In the process of the present invention, a nitrogen monoxide gas is brought into contact with an aqueous solution of an alkyl alcohol and nitric acid while allowing nitric acid to react with nitrogen monoxide and the alkyl alcohol, to produce an alkyl nitrite.

In the aqueous solution, there is no limitation to the concentration of nitric acid. Usually, nitric acid is preferably contained in a concentration of 60% by mass or less, more preferably 1 to 60% by mass, more preferably 1 to 20% by mass, in the aqueous solution.

The alkyl alcohol usable for the process of the present invention preferably has 1 to 3 carbon atoms, and is more preferably selected from methyl alcohol, ethyl alcohol n-propyl alcohol and isopropyl alcohol, still more preferably methyl alcohol.

In the aqueous solution, the alkyl alcohol is preferably contained in a concentration of 5 to 70% by mass, more preferably 15 to 60% by mass, still more preferably 20 to 55% by mass.

The aqueous solution containing nitric acid and the alkyl alcohol may be a liquid fraction obtained, as a by-product, from a process in which an alkyl alcohol is reacted with nitrogen monoxide and oxygen to produce an alkyl nitrite, as disclosed in JP-11-189,570-A and JP-6-298,706-A. In this case, the aqueous solution (the liquid fraction) preferably contains nitric acid in a concentration of 20% by mass or less, more preferably 1 to 20% by mass, still more preferably 2 to 15% by mass, and the non-reacted alkyl alcohol in a concentration of 15 to 60% by mass, more preferably 20 to 55% by mass.

The nitrogen monoxide gas usable for the process of the present invention, preferably contains nitrogen monoxide in a content of 4 to 100% by volume. Usually, in the nitrogen monoxide gas, nitrogen monoxide is diluted with a dilute gas non-reactive with nitrogen monoxide, for example, nitrogen gas. The nitrogen monoxide gas may contain a gas component which does not obstruct the alkyl nitrite-producing reaction for the process of the present invention. Namely, the non-obstructive gas component may comprise carbon monoxide, carbon dioxide and alkyl alcohol vapors. However, to produce the target alkyl nitrite from nitric acid with a high efficiency, the nitrogen monoxide gas is preferably substantially free from nitrogen oxides produced by the presence of molecular oxygen contained in the nitrogen monoxide gas. Namely, the nitrogen monoxide is preferably substantially free from nitrogen dioxide, dinitrogen trioxide, dinitrogen tetraoxide and molecular oxygen. Also, the aqueous solution of the alkyl alcohol and nitric acid is more preferably free from the above-mentioned nitrogen oxides.

In the process of the present invention, nitrogen monoxide is preferably fed in an amount of 1 to 50 moles, more preferably 1.5 to 20 moles, still more preferably 2 to 10 moles per mole of nitric acid into the reaction system.

In the process of the present invention, the reaction procedure of nitric acid with nitrogen monoxide and the alkyl alcohol is preferably carried out at a temperature of 0 to 200° C., more preferably 20 to 100° C. The reaction pressure is preferably the ambient atmospheric pressure or more, but not more than 20 MPa G, more preferably not more than 3 MPa G, still more preferably 0.2 to 1 MPa G. The reaction procedure of the process of the present invention can be carried out under pressurized conditions as mentioned above.

In the process of the present invention, the reaction procedure of nitric acid with nitrogen monoxide and the alkyl alcohol in an aqueous medium is optionally carried out in the presence of a catalyst. Namely, the aqueous solution of nitric acid and the alkyl alcohol optionally further contain a catalyst comprising at least one nitrate salt of Group VIII metals, except for platinum group metals, and of Group IB metals of the Periodic Table. The nitrate salts of Group VIII metals for the catalyst are preferably selected from, for example, ferric nitrate, nickel nitrate and cobalt nitrate. As a nitrate salt of Group IB metals for the catalyst, cupric nitrate is preferably employed. The catalyst is preferably present in a content, in term of metal, of 20% by mass or less, more preferably 0.1 to 10% by mass, based on the total mass of the aqueous solution containing nitric acid and alkyl alcohol.

The reaction procedure of nitric acid with nitrogen monoxide and the alkyl alcohol is carried out in liquid phase in a batch type reactor or a continuous type reactor. The reaction procedure is conducted by the steps of placing an aqueous solution containing nitric acid together with an alkyl alcohol in a reaction vessel equipped with a stirrer; and introducing a nitrogen monoxide gas into the aqueous solution under the ambient atmospheric air pressure or higher, while stirring the aqueous solution or blowing a nitrogen monoxide gas into the aqueous solution under a pressure higher than the ambient atmospheric pressure while stirring the aqueous solution under the higher pressure. In this procedure, preferably substantially no nitrogen oxides are produced due to the presence of molecular oxygen gas contained in the nitrogen monoxide gas, thus are contained in the nitrogen monoxide gas, and are fed into the reaction system in the reactor. There is no specific limitation to the reactor as long as the target reaction can be carried out with satisfactory efficiency in the reactor and the reactor can have a single reaction section or a plurality of reaction sections or a plurality of reactors are connected to each other to constitute a reaction system. The reactor may be in the form of a reaction vessel with a stirrer, or a multistage type reaction column, for example, a packed reaction column or a sieve tray reaction column. However, as the reaction for the process of the present invention is of a gas-liquid contact type, when the vessel type reactor equipped with a stirrer is used, the stirring apparatus is preferably provided with an impeller capable of dispersing gas bubbles in the aqueous solution with a high efficiency and a rotary means for the impeller capable of enhancing the gas-liquid contact efficiency; and when the multistage type reactor column is used, the column preferably is packed with a packing material capable of enhancing the gas-liquid contact efficiency.

The resultant alkyl nitrite ester is delivered together with the above-mentioned gas, as a gas fraction, from the reactor to the outside of the reactor, and is optionally washed and refined and then supplied to a desired use.

In an embodiment of the process of the present invention, the process of the present invention is utilized for a process for producing an alkyl nitrite ester in which process, an alkyl alcohol is reacted with nitrogen monoxide and oxygen, to enhance the yield of the target alkyl nitrite ester. In this case, nitric acid produced, as a by-product of the above-mentioned process, is utilized for the process of the present invention.

In this embodiment, (A) the aqueous solution of the alkyl alcohol and nitric acid is prepared in a reaction column by procedures such that the alkyl alcohol is fed into a top portion of the reaction column while allowing the fed alkyl alcohol to fall down through the reactor column; nitrogen monoxide and oxygen gasses are fed separately or together into a bottom portion of the reaction column while allowing the fed nitrogen monoxide and oxygen gases to flow upward through the reaction column and to react with the falling alkyl alcohol; the resultant gas fraction containing alkyl nitrite gas is delivered through a top outlet of the reaction column and the resultant liquid fraction containing the non-reacted alkyl alcohol and nitric acid dissolved in water is collected in a bottom portion of the reaction column; and the collected liquid fraction is withdrawn from the bottom portion of the reaction column and a portion of the withdrawn liquid fraction is fed into a reactor, and (B) in the reactor, a nitrogen monoxide gas is brought into contact with the fed liquid fraction, to produce an alkyl nitrite.

In the reactor, preferably, oxygen and nitrogen dioxide are not fed.

Preferably, a gas fraction produced in the reactor and containing the alkyl nitrite is withdrawn from the reactor and introduced into a portion located between the bottom and middle portions of the reaction column, the introduced gas fraction is allowed to flow upward, together with the gas fraction produced in the reactor column, through the reactor column and to be refined with the falling down alkyl alcohol, and the refined alkyl nitrite gas is delivered through the top outlet of the reaction column.

The embodiment of the process of the present invention will be further explained with reference to the attached drawings.

Referring to FIG. 1, a reaction column 1 for producing an alkyl nitrite ester has an upper section 1a, a lower section 1b, a bottom portion 1c located below the lower section 1b, a top portion 1d located above the upper section 1a and a middle portion 1e located between the upper and lower sections 1a and 1b, connected to each other. The reaction column 1 is connected to a reactor 2 through a pipe line 3 through which the bottom portion 1c of the reaction column 1 is connected to a middle portion 2a of the reactor 2. The top portion 1d of the reaction column 1 is connected to a pipe line 4 connected to a supply source (not shown in FIG. 1) of a liquid alkyl alcohol. Also, the top portion 1d is connected to a pipe line 5 for withdrawing and optionally circulating a gas fraction generated in the reaction column 1. The pipe line 5 has a branched pipe line 6 for discharging a portion of the gas fraction to the outside of the reaction system.

The bottom portion 1c of the reaction column 1 is connected at an upper part thereof to a supply source (not shown) of nitrogen monoxide gas through a pipe line 7 and a supply source (not shown) of oxygen gas through a pipe line 7a.

The pipe line 3 is connected at a middle part thereof to a pipe line 8 having a cooler 9 located in a middle portion of the line 8 and connected to the middle portion 1e of the reaction column 1.

The reactor 2 has a pipe line 10 through which a top portion 2b of the reactor 2 is connected to the pipe line 7, to feed a gas fraction generated in the reactor 2 into the upper part of the bottom portion 1c of the reaction column 1. Also, a bottom portion 2c of the reactor 2 is connected to a supply source (not shown) of nitrogen monoxide gas through a pipe line 11. Further, the bottom of the reactor 2 is connected to a pipe line 12 for withdrawing a liquid fraction generated in the reactor 2.

Referring to FIG. 1, a liquid alkyl alcohol is fed into the top portion 1d of the reaction column 1 to allow the liquid alkyl alcohol to fall down through the upper and lower sections 1a and 1b of the reaction column 1. Simultaneously, a nitrogen monoxide gas and an oxygen gas or a nitrogen monoxide-oxygen mixed gas is fed into the upper part of the bottom portion 1c through the pipe lines 7 and 7a so that the fed nitrogen monoxide and oxygen gasses flow upward through the reaction column 1 and come into contact with and react with the falling liquid alkyl alcohol, to produce the alkyl nitrite in a gas phase. The resultant gas fraction (a) containing the alkyl nitrite is washed or refined with the falling alkyl alcohol and withdrawn from a top outlet of the top portion 1d of reaction column 1 through a pipe line 5. Also, the resultant liquid fraction containing non-reacted alkyl alcohol and nitric acid generated as a by-product of the above-mentioned reaction and dissolved in water, which is a by-product of the reaction, in the reaction column 1 is accumulated in the bottom portion 1c of the reaction column 1. The liquid fraction (b) is withdrawn from the bottom portion 1c and a portion (b-1) of the withdrawn liquid fraction (b) is fed into the middle portion 2a of the reactor 2 through a pipe line 3, and another portion (b-2) of the withdrawn liquid fraction (b) is recycled through the pipe line 8 and the cooler 9 into the middle portion 1e of the reaction column 1. The cooled, and recycled liquid fraction (b-2) falls down together with the falling liquid alkyl alcohol through the lower section 1b of the reaction column (1), to control the reaction temperature of the alkyl alcohol with nitrogen monoxide and oxygen to a desired level.

The portion (b-1) of the liquid fraction (b) fed into the reactor 2 is brought into contact with the nitrogen monoxide gas fed into the bottom portion 2c of the reactor 2 through the pipe line 11. Thus nitric acid contained in the portion (b-1) of the liquid fraction (b) reacts with the fed nitrogen monoxide and the non-reacted alkyl alcohol, to produce an alkyl nitrite in a gas phase. A resultant gas fraction (c) containing the target alkyl nitrite and the non-reacted nitrogen monoxide is withdrawn from the top outlet of the top portion 2b of the reactor 2 through the pipe line 10 and fed into the upper part of the bottom portion 1c of the reaction column 1 through the pipe line 7. The fed gas fraction (c) flows upward together with the nitrogen monoxide and oxygen gasses through the reaction column 1, and the non-reacted nitrogen monoxide and oxygen in the gas fraction (c) reacts with the falling alkyl alcohol and the resultant alkyl nitrite and the alkyl nitrite in the gas fraction (c) are washed or refined with the falling down alkyl alcohol and delivered together with the gas fraction (a) from the reaction column 1 through the top portion 1d through the pipe line 5. The liquid fraction (d) accumulated in the bottom portion 2c of the reactor 2 is optionally withdrawn through the pipe line 12.

Figure 2:
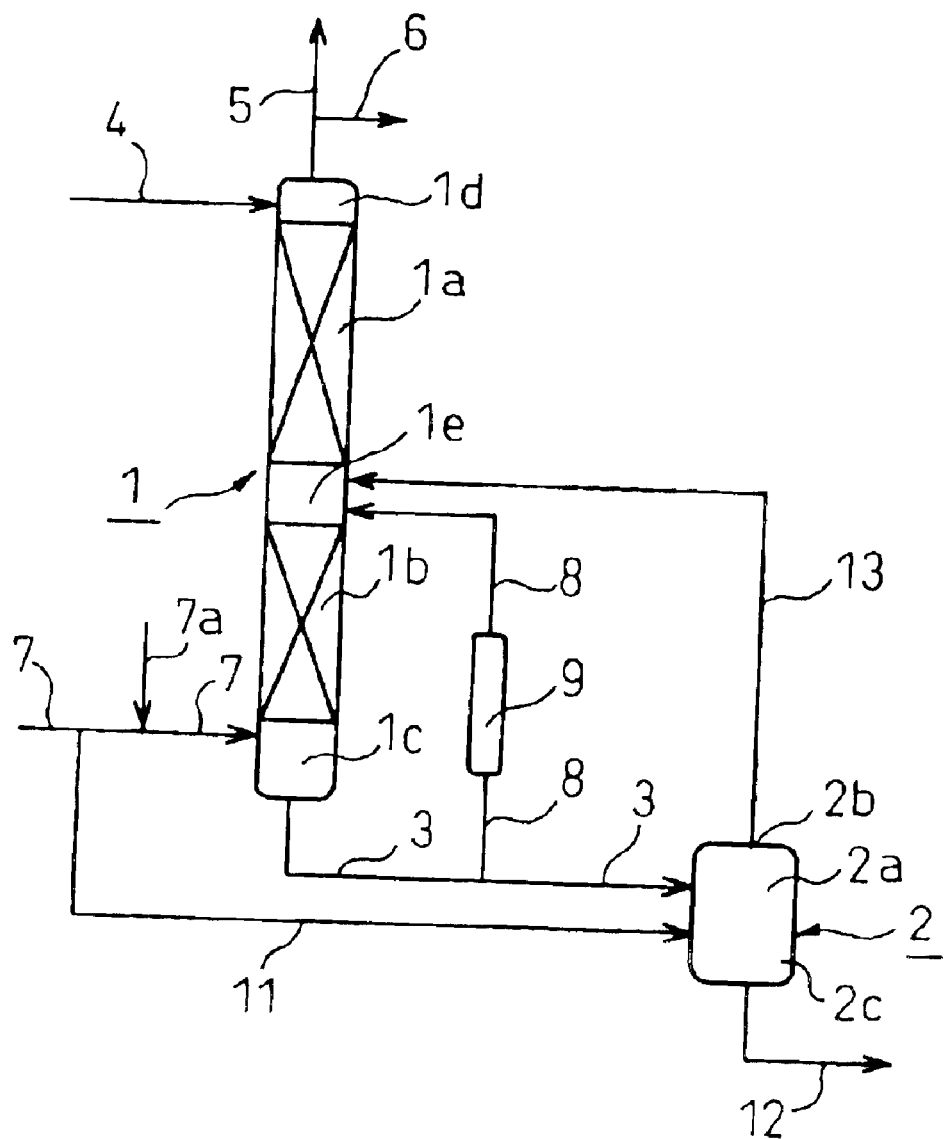
FIG. 2 is a flow sheet showing another embodiment of the process of the present invention for producing an alkyl nitrite.

Referring FIG. 2, the same reaction procedures as in FIG. 1 are carried out, except that the gas fraction (c) generated in the reactor 2 is withdrawn from the top outlet of the top portion 2b of reactor 2 through a pipe line 13 and fed into the middle portion 1e of the reaction column 1.

In the above-mentioned embodiment of the process of the present invention, the nitrogen monoxide gas for the reactor 2 may be supplied separately from the nitrogen monoxide gas for the reaction column 1. However, preferably, the nitrogen monoxide gas is fed from a common supply source to both the reaction column 1 and the reactor 2. In this case, referring to FIGS. 1 and 2, the supply line of nitrogen monoxide gas from a common supply source (not shown) is preferably divided into both of the pipe line 7 connected to the reaction column 1 and the pipe line 11 connected to the reactor 2. The nitrogen monoxide gas is preferably substantially free from nitrogen oxides produced due to the presence of molecular oxygen in the nitrogen monoxide gas.

The gas fraction (c) generated in the reactor 2 and withdrawn from the top portion 2b of the reactor 2 is preferably fed into a portion of the reaction column 1 through which portion the liquid alkyl alcohol falls, more preferably a portion between the middle portion 1e and the bottom portion 1c of the reaction column 1. When the gas fraction (c) withdrawn from the reactor 2 is introduced into the middle portion 1e of the reaction column 1 through the pipe line 13 shown in FIG. 2, the portion (b-2) of the liquid fraction withdrawn from the bottom portion 1c and cooled by the cooler 9 is preferably fed at a location below the location at which the gas fraction (c) from the reactor 2 is introduced into the middle portion 1e of the reaction column 1 through the pipe line 13, so that the gas fraction (c) fed into the reaction column can flow upward without contacting the liquid fraction (b-2) and can be washed or refined with the falling alkyl alcohol in the upper portion 1a of the reaction column 1.

The nitrogen monoxide gas to be fed into the reaction column 1 may contain nitrogen dioxide, dinitrogen trioxide and/or dinitrogen tetraoxide. In this case, the content, in terms of gram atoms of nitrogen, of nitrogen monoxide in the gas is more than 50% based on the total amount, in terms of gram atoms of nitrogen, of nitrogen monoxide, nitrogen dioxide, dinitrogen trioxide and dinitrogen tetraoxide.

The oxygen (molecular oxygen) is preferably employed in an amount of 0.02 to 0.25 mole, more preferably 0.05 to 0.20 mole, per mole of nitrogen monoxide, for the reaction in the reaction column 1.

For the reaction column 1, nitrogen monoxide and molecular oxygen are usually mixed with a gas non-reactive with the alkyl alcohol, oxygen, nitrogen monoxide and the reaction products in the reaction column 1, for example, nitrogen or carbon dioxide, and the mixed gas is fed, as a material gas into the bottom portion 1c of the reaction column 1. In this case, the material gas preferably has a total content of nitrogen monoxide and oxygen of 3 to 40% by volume, more preferably 5 to 20% by volume, and a content of the non-reactive gas of 10 to 90% by volume, more preferably 20 to 80% by volume. The material gas for the reaction column 1 may contain an alkyl alcohol in the state of a mist or vapor, in a content of 2 to 40% by volume, and further carbon monoxide and/or an alkyl nitrite.

The nitrogen monoxide gas may be mixed with the oxygen gas and optionally a non-reactive gas in the above-mentioned mixing proportions outside the reaction column 1, and the resultant mixed gas is fed into the reaction column 1. Alternatively, the nitrogen monoxide gas and the oxygen gas may be separately fed into an upper part of the bottom portion $1c$. In this case, the nitrogen monoxide gas for the reaction column 1 is preferably supplied from a common supply source for the reactor 2.

The alkyl alcohol to be fed into the reaction column 1 is preferably selected from alkyl alcohols having 1 to 3 carbon atoms, for example, methyl alcohol and ethyl alcohol and propyl alcohols, more preferably methyl alcohol, and an alkyl nitrite is produced in response to the alkyl alcohol fed into the reaction column. The alkyl alcohol is optionally cooled and preferably fed at a temperature of $-15°$ C. to $50°$ C., more preferably $-10°$ C. to $30°$ C.

As mentioned above, preferably, the alkyl alcohol is fed into a top portion of the reaction column and allowed to fall down through the reaction column, and the nitrogen monoxide gas and the molecular oxygen gas are fed into a bottom portion of the reaction column and allowed to flow upward through the reaction column and to come into contact with the falling alkyl alcohol. Thus, a gas-liquid contact reaction in a countercurrent relationship occurs in the reaction column.

The feed rate in terms of mole of the alkyl alcohol into the reaction column is preferably 0.2 to 3.0 times, more preferably 0.3 to 2.0 times the total feed rate in terms of mole, of the nitrogen oxides including nitrogen monoxide and another all nitrogen oxides produced from nitrogen monoxide and oxygen in the material gas fed into the reaction column and nitrogen monoxide introduced from the reactor into the reaction column. Also, in the embodiment of the process of the present invention, a portion of the alkyl alcohol to be fed into the reaction column may be fed in the state of a mist or vapor into the bottom portion of the reaction column through the pipe line for the nitrogen monoxide gas or nitrogen monoxide-oxygen mixed gas or through an other pipe line than the above-mentioned pipe line for the nitrogen monoxide gas or the nitrogen monoxide-oxygen mixed gas, while the composition of the material gas is maintained in the above-mentioned range.

In the reaction column, the reaction temperature of the alkyl alcohol with nitrogen monoxide and oxygen is preferably controlled to 0 to $100°$ C., more preferably 5 to $80°$ C., still more preferably 10 to $60°$ C. In the embodiment of the process of the present invention, preferably, the liquid fraction accumulated in the bottom portion of the reaction column is withdrawn by a liquid-transportation means, for example, a pump (not shown in FIGS. 1 and 2), a major portion of the withdrawn liquid fraction is introduced into a cooler to cool the liquid fraction to a desired temperature, the cooled liquid fraction is returned into a portion of the reaction column located between the middle portion and the bottom portion of the reaction column, to allow the cooled liquid fraction to fall down. This liquid fraction-circulating procedure is preferably carried out continuously, more preferably, continuously and simultaneously with the above-mentioned reaction procedure of the alkyl alcohol with nitrogen monoxide and oxygen. The withdrawn and cooled portion of the liquid fraction contributes to removing the reaction heat generated in the lower section and the bottom portion of the reaction column and maintaining the reaction temperatures of the lower section within a desired range. The amount of the portion of the liquid fraction to be fed into the circulation system is established so that the above-mentioned contribution can be attained.

In the liquid fraction-circulation procedure, (a) the circulation rate in terms of mass of the liquid fraction, in the other words, the returning rate in terms of mass of the withdrawn liquid fraction into the reaction column, is preferably controlled to 50 to 300 times, more preferably 60 to 180 times, still more preferably 70 to 160 times, the feed rate in terms of mass of the alkyl alcohol into the reaction column; (b) a total feed rate in terms of mole of the alcohol fed into the reaction column and the non-reacted alkyl alcohol contained in the returned liquid fraction into the reaction column is preferably controlled to 20 to 150 times, more preferably 30 to 120 times, the total feed rate, in terms of mole, of whole the nitrogen oxides fed into the reaction column; and (c) the concentration of non-reacted alkyl alcohol contained in the liquid fraction collected in the bottom portion of the reaction column is preferably controlled to 15 to 60% by mass, more preferably 20 to 55% by mass.

In the circulation procedure, the portion of the withdrawn liquid fraction is preferably cooled to a temperature of 0 to $60°$ C. and 1 to $20°$ C., more preferably 3 to $10°$ C. below the temperature of the withdrawn liquid fraction before cooling. When the circulation procedure of the portion of the withdrawn liquid fraction from the reaction column is carried out so that the above-mentioned requirements (a), (b) and (c) are satisfied, the reaction heat generated in the lower section $1b$ can be removed with high efficiency, the production of nitric acid can be restricted to a low level, and thus the above-mentioned gas-liquid contact reaction can be effected with a high efficiency.

The above-mentioned feed rate of the alkyl alcohol into the reaction column means a total feed rate of the alkyl alcohol fed in the states of liquid and a vapor and/or mist from the outside into the reaction column. For example, referring to FIGS. 1 and 2, the feed rate is of a total of the liquid alkyl alcohol fed into the top portion $1d$ of the reaction column 1 through the pipe line 4, the alkyl alcohol fed in the state of a vapor or mist into the bottom portion $1c$ of the reaction column 1 through a pipe line 7, together with the nitrogen monoxide gas, and the alkyl alcohol contained in the gas fraction generated in the reactor 2 and fed into the reaction column 1 at a location between the middle portion $1e$ and the bottom portion $1c$ thereof through the pipe line 10 or 13. However, the alkyl alcohol contained in the portion of the withdrawn liquid fraction and fed into the middle portion $1e$ of the reaction column 1 through the pipe line 8 is not involved in the calculation of the total feed rate of the alkyl alcohol into the reaction column 1.

The content in terms of mole of the alkyl alcohol in the liquid fraction collected in the bottom portion $1c$ of the reaction column 1 is preferably 0.5 to 6.0 times, more preferably 1.0 to 5.0 times, the feed rate in terms of mole, of whole the nitrogen oxides fed into the reaction column 1.

Referring to FIGS. 1 and 2, the reaction column 1 necessarily has a lower section $1b$ in which the reaction (1) of the alkyl alcohol with nitrogen monoxide and oxygen is carried out and an upper section $1a$ in which water produced as a by-product of the above-mentioned reaction (1), and contained, together with the alkyl nitrite, in the resultant gas fraction (a). Preferably, the upper section 1a is connected to the lower section 1b through a middle portion 1e having an appropriate length.

The upper portion 1a is not limited to a specific type, as long as the alkyl alcohol can fall down through the upper section 1a and the falling down alkyl alcohol can absorb moisture contained in the gas fraction produced in the reaction column 1 and flowing upward through the upper section 1a. For example, the upper section 1a may have a multistage distillation column structure having a plurality of trays, for example, sieve trays or valve trays or a packed column structure in which packing materials, for example, Raschig rings or Pall rings, are packed. There is no limitation to the structure and type of the lower section 1b as long as the reaction (1) of the alkyl alcohol with nitrogen monoxide and oxygen can be effected with a satisfactory efficiency. For example, the lower section 1b may have a multiple stage distillation column structure or a packed column structure similar to that of the upper section 1a.

Namely, the reaction column 1 preferably has an upper section 1a having a multistage distillation column structure or a packed column structure and a lower section 1b having a packed column structure and further a middle portion 1e formed between the upper and lower sections 1a and 1b and having an appropriate length, the upper section 1a, the middle portion 1e and the lower section 1b being connected with each other to form a body of reaction column, as shown in FIG. 1 or 2.

In the reaction apparatus shown in FIG. 1 or 2, preferably, the liquid fraction (b) accumulated in the bottom portion 1c of the reaction column 1 is continuously withdrawn through a pipe line 3, a minor portion (b-1) of the withdrawn liquid fraction (b) is continuously or periodically introduced into a reactor 2 through a pipe line 3, and a major portion (b-2) of the withdrawn liquid fraction (b) is continuously cooled in the cooler 9 and returned into the middle portion 1e of the reaction column 1 through the pipe line 8. In the reactor 2, nitric acid contained as a by-product in the portion (b-2) of the liquid fraction (b) reacts with nitrogen monoxide fed through the pipe line 11 and with the non-reacted alkyl alcohol in the portion (b-2), in accordance with the process of the present invention. In this case, the feed rate of the liquid fraction (b) into the reactor 2 is preferably controlled so that the level of the liquid fraction accumulated in the bottom portion 1c of the reaction column 1 is maintained constant.

The content of the non-reacted alkyl alcohol in the liquid fraction (b) is controlled as mentioned above, and thus the content of the non-reacted alkyl alcohol contained in the portion (b-1) of the withdrawn liquid fraction to be introduced into the reactor 2 is preferably controlled to 15 to 60% by mass, more preferably 20 to 55% by mass. Also, the content of nitric acid contained in the portion (b-1) of the liquid fraction (b) is not specifically limited and may be 60% by mass or less. As it is preferred that the alkyl nitrite is produced with a high efficiency in the reaction column 1 by the circulation procedure of the withdrawn liquid fraction, the content of nitric acid in the withdrawn liquid fraction (b) is preferably controlled to 20% by mass or less, more preferably 1 to 20% by mass, still more preferably 2 to 15% by mass. The withdrawn liquid fraction (b) of the reaction column 1 contains water produced as a by-product of the reaction of the alkyl alcohol with nitrogen monoxide and oxygen and a small amount of alkyl nitrite.

In the reactor 2, a nitrogen monoxide gas is introduced into the liquid fraction (b-2) received in the reactor 2 through a pipe line 11 and the reaction of the nitric acid with nitrogen monoxide and the alkyl alcohol is carried out under the ambient atmospheric pressure or higher, while stirring the liquid fraction. Alternatively, the nitrogen monoxide gas is introduced into the reactor 2 and the reaction is carried out under pressure above the ambient atmospheric pressure, while stirring the liquid fraction (b-2). In this reaction, preferably the nitrogen monoxide gas and the liquid fraction fed into the reactor 2 are substantially free from nitrogen oxides produced due to the presence of molecular oxygen in the nitrogen monoxide gas. The reaction is carried out in liquid phase and the reactor 2 may be of a batch type or a continuous type.

The nitrogen monoxide to be fed into the reactor 2 may be a pure nitrogen monoxide gas or a mixed gas in which nitrogen monoxide is diluted with a non-reactive gas, for example, nitrogen gas or an inert gas. Preferably, the pipe line 11 for feeding the nitrogen monoxide gas into the reactor 2 is connected to a pipe line 7 connected to a nitrogen monoxide gas-supply source (not shown in FIGS. 1 and 2) at a location upstream of a location at which the pipe line 7a for feeding an oxygen gas is connected to the pipe line 7, to prevent contamination, by oxygen, of the nitrogen monoxide gas to be fed into the reactor 2.

The molar amount of the nitrogen monoxide to be fed into the reactor 2 must be equal to or more than the molar amount of nitric acid contained in the liquid fraction (b-1) in the reactor 2. In the case where the nitrogen monoxide gas fed into the reactor 2 is supplied from a common supply source for the nitrogen monoxide to be fed into the bottom portion 1c of the reaction column 1, for example, where an alkyl nitrite ester is produced while a large amount of nitrogen monoxide is circulated through a production system in which the alkyl nitrite-production system is combined with a dialkyl oxalate production system, the feed rate of the nitrogen monoxide gas into the reactor 2 is preferably controlled in such a range that the reaction of the alkyl alcohol with nitrogen monoxide and oxygen in the reaction column and the reaction of the alkyl alcohol with nitrogen monoxide and nitric acid in the reactor and other production procedures are not hindered. Where the nitrogen monoxide gas for the reactor 2 is supplied from a supply source other than that for the reaction column 1, the molar amount of the fed nitrogen monoxide is 1 to 50 times the molar amount of nitric acid contained in the liquid fraction introduced in the reactor 2.

In the reactor 2, the reaction temperature of nitric acid with nitrogen monoxide and the alkyl alcohol is preferably 0 to 200° C., more preferably 20 to 100° C., and the reaction pressure is preferably the ambient atmospheric pressure or more but not more than 20 MPa G, more preferably not more than 3 MPa G, still more preferably 0.2 to 1 MPa G. Namely, the reaction in the reactor 2 may be effected under pressure.

The reaction in the reactor 2 is optionally carried out in the presence of a catalyst comprising at least one nitrate salt of Group VIII metals except for platinum group metals and of Group IB metals of the Periodic Table. The Group VIII metal nitrates are preferably selected from ferric nitrate, nickel nitrate and cobalt nitrate, and as a Group IB metal nitrate, cupric nitrate is preferably employed. The catalyst is preferably present in a content, in terms of metal, of 20% by mass or less, more preferably 0.1 to 10% by mass, in the liquid fraction contained in the reactor 2. The reactor 2 is not limited to a specific form or constitution, as long as the reaction of nitric acid with nitrogen monoxide and the alkyl alcohol can be effected with a satisfactory efficiency in the reactor 2.

The reactor 2 may have a single reaction space or a plurality of reaction sections or may be constituted from a single reactor or a plurality of reactors connected with each other in series or in parallel. The reactor 2 may be in the form of a reaction vessel with a stirrer, or a multistage reaction column, for example, a packed reaction column or a sieve tray reaction column. As the reaction is a gas-liquid contact reaction, when a stirrer-equipped reaction vessel is used as a reactor 2, the stirring apparatus must be provided with an impeller and a rotary means capable of stirring the reaction system with a high stirring efficiency and a high gas-dispersing efficiency, and exhibit a high gas-liquid contact efficiency. When a multistage reaction column is used, a packing material having a high gas-liquid contact efficiency is preferably packed therein.

In the reactor 2, the resultant gas fraction (c) containing the target alkyl nitrite produced by the conversion of nitric acid is withdrawn through the top outlet 2b of the reactor 2 and introduced into a portion of the reaction column 1 through which portion the alkyl alcohol falls down, preferably which portion includes the middle portion 1e, the lower section 1b and the bottom portion 1c of the reaction column 1, through the pipe lines 10 and 7 of FIG. 1 or the pipe line 13 of FIG. 2. In the case where the amount of the nitrogen monoxide gas introduced into the reactor 2 is not too large, the gas fraction (c) is introduced into either middle portion 1e or the lower section 1b of the reaction column 1, preferably into the middle portion 1e, more preferably at a location of the middle portion 1e above the location at which the circulated portion (b-2) of the liquid fraction (b) is introduced into the middle portion 1c through the pipe line 8. In the case where the nitrogen monoxide is introduced in a large amount into the reactor 2, preferably, the gas fraction (c) containing the alkyl nitrite is directly introduced into an upper part of the bottom portion 1c or into the pipe line 7 at a location upstream to the location at which the pipe line 7a for oxygen is connected to the pipe line 7 and downstream from the location at which the pipe line 11 for feeding nitrogen monoxide to the reactor 2 is connected to the pipe line 7 as shown in FIG. 1, so that the gas fraction (c) is mixed with the nitrogen monoxide gas and then with the oxygen gas and the resultant mixed gas is introduced into the bottom portion 1c of the reaction column 1. The pipe line 7 is preferably connected to an upper part of the bottom portion 1c.

The reaction system shown in FIG. 1 or 2 is very useful for various synthesis reactions using carbon monoxide and an alkyl nitrite ester, for example, for a production of a dialkyl oxalate ester or a dialkyl carbonate ester. The reaction system enables the dialkyl oxalate ester or a dialkyl carbonate ester to be continuously produced with a high space time yield and in a high selectivity, by a process shown in FIG. 3.

In the process shown in FIG. 3, a reactor 21 for producing a dialkyl oxalate ester (which will be referred to reactor 21 hereinafter) is connected at an end portion thereof to a pipe line 22 for feeding a carbon monoxide gas into the reactor. Also, the reactor 21 is connected to the pipe line 5 for delivering the gas fraction containing an alkyl nitrite from the top portion 1d of the reaction column 1. Further the reactor 21 is connected at another end portion thereof to a pipe line 23 for withdrawing a gas fraction (e) generated in the reactor 21. The pipe line 23 is connected to a lower portion of an absorption column 24 connected at an upper portion thereof to a pipe line 24 for feeding an absorption liquid comprising a liquid alkyl alcohol. The absorption column 24 is connected at a bottom portion thereof to a pipe line 25 for withdrawing a liquid fraction generated in the absorption column 24. The top portion of the absorption column 24 is connected to the pipe line 7. In the reactor 21, a platinum group metal catalyst is contained.

Figure 3:
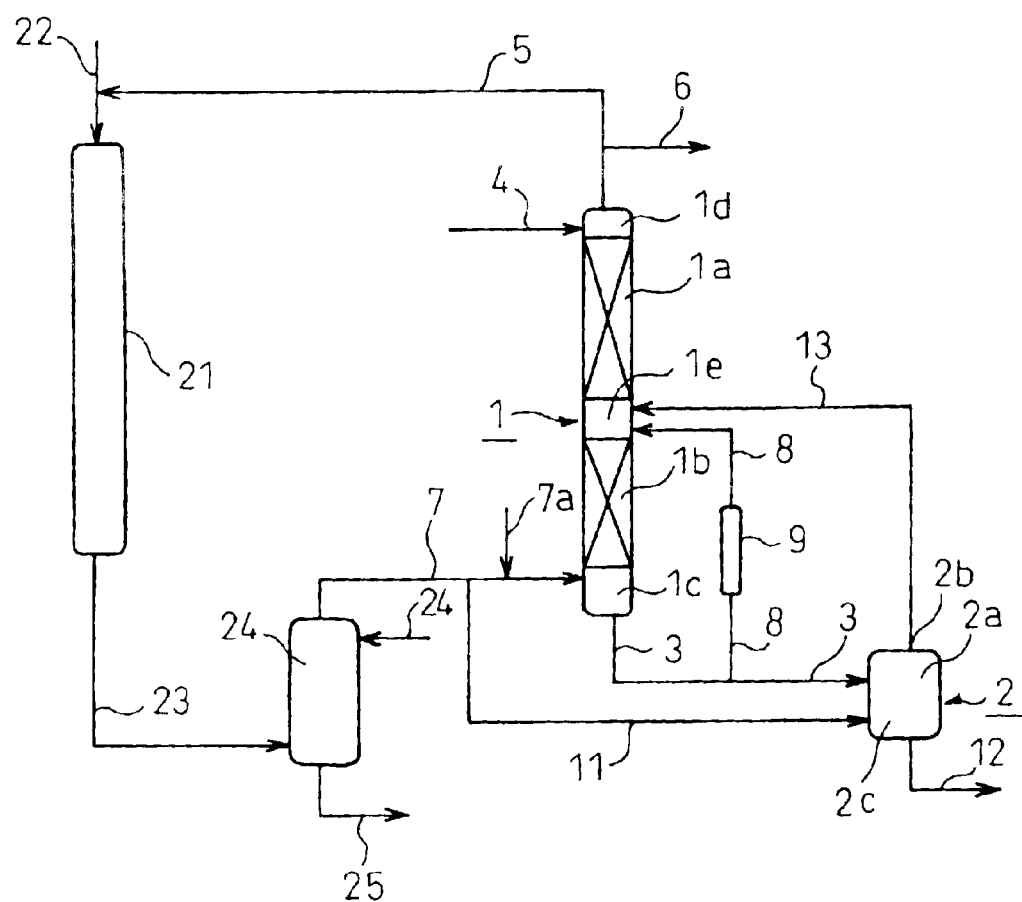
FIG. 3 is a flow sheet showing a process for producing a dialkyl oxalate, utilizing an embodiment of the process of the present invention for producing an alkyl nitrite.

Referring to FIG. 3, the gas fraction (a) generated in the reaction column 1 and containing an alkyl nitrite is fed into the reactor 21 through the pipe line 5 and a carbon monoxide gas is fed into the reactor 21 through the pipe line 22. In the reactor 21, carbon monoxide reacts with the alkyl nitrite in the presence of a platinum group metal catalyst, to produce a dialkyl oxalate ester. The resultant gas fraction containing the dialkyl oxalate ester is withdrawn from the reactor 21 and fed into the bottom portion of the absorption column 24 through the pipe line 23. The fed gas fraction (e) is allowed to flow upward through the absorption column 24. An absorption liquid comprising a liquid alkyl alcohol is fed into the upper portion of the absorption column 24 and allowed to fall down through the absorption column 24. The flowing gas fraction (e) comes into contact with the falling absorption liquid in countercurrent relationship, to allow the dialkyl oxalate ester to be extracted and concentrated in the absorption liquid. The resultant liquid fraction (f) comprising the dialkyl oxalate ester extracted in the absorption liquid is withdrawn from the absorption column 24 through the pipe line 25 and subjected to a procedure for isolating the target dialkyl oxalate ester from the absorption liquid by using a distillation column (not shown in FIG. 3).

Also, a resultant gas fraction (g) generated in the absorption column 24 and containing nitrogen monoxide produced as a by-product of the reaction carried out in the reactor 21, non-reacted carbon monoxide, the alkyl alcohol vapor, and non-reactive dilution gas, is withdrawn from the top portion of the absorption column 24 and fed, as a nitrogen monoxide-containing material gas, into the bottom portion 1c of the reaction column 1 through the pipe line 7, together with the oxygen gas fed through the pipe line 7a. In this case, the reaction column 1 serves as an alkyl nitrite-regeneration column.

Referring to FIG. 3, an alkyl alcohol is fed into the top portion 1d of the reaction column 1 through a pipe line 4 and falls down through the reaction column 1. The material gas containing nitrogen monoxide and oxygen and fed into the bottom portion 1c of the reaction column 1 flow upward through the reaction column 1 and comes into contact with the falling alkyl alcohol in a countercurrent relationship and a gas-liquid reaction is carried out to regenerate an alkyl nitrite. The resultant gas fraction (a) containing the alkyl nitrite is withdrawn from the top portion 1d of the reaction column 1 and introduced into the reactor 21 through the pipe line 5. Optionally, a portion of the withdrawn gas fraction (a) is discharged through a pipe line 6.

The resultant liquid fraction (b) containing the non-reacted alkyl alcohol and nitric acid produced as a by-product is accumulated in the bottom portion 1c of the reaction column 1 and continuously withdrawn from the bottom portion 1c through a pipe line 3. A portion of the withdrawn liquid fraction is circulated through a cooler 9 and a pipe line 8 and returned into the middle portion 1e of the reaction column 1 and the remaining portion of the withdrawn liquid fraction (b) is fed into the upper portion 2a of the reactor 2 and brought into a reaction with nitrogen monoxide gas fed into the bottom portion 2c of the reactor 2 through the pipe line 11. The reaction of nitric acid with nitrogen monoxide and the alkyl alcohol in the rector 2 is preferably carried out while feeding a nitrogen monoxide gas substantially free from nitrogen oxides produced due to the presence of molecular oxygen contained in the nitrogen monoxide gas. The resultant gas fraction (c) containing an alkyl nitrite is withdrawn through the top outlet of the reactor 2 and fed into the bottom portion 1c or middle portion 1e of the reaction column 2 through which portion the alkyl alcohol falls down, through the pipe lines 10 and 7 or the pipe line 13. The withdrawn gas fraction (c) may be directly fed into the bottom portion 1c of the reaction column 1. The fed gas fraction (c) is washed or refined by the falling alkyl alcohol and withdrawn, together with the gas fraction (a) from the reaction column 1 and fed into the reactor 21 through the pipe line 5. In this case, the nitric acid produced, as a by-product, in the reaction column 1 can be utilized as a component for producing an alkyl nitrite in the reactor 2, with a high efficiency and can reduce the loss of nitrogen component due to a discharge of the liquid fraction (b) containing nitric acid and/or the gas fraction (a) containing an alkyl nitrite and nitrogen monoxide. Thus, the amount of the nitrogen component to be supplemented into the reaction system can be decreased by the above-mentioned simple specific reaction system.

EXAMPLES

The process of the present invention will be further illustrated in detail by the following examples.

In the examples and comparative examples, the content of nitric acid is determined by an ion chromatography and a titration and the contents of another compounds are determined by a gas chromatography.

Example 1

An autoclave made from SUS 316, having a capacity of one liter and equipped with a stirrer having four paddle type impeller, a gas-supply nozzle a gas-withdrawing nozzle, and a liquid-withdrawing nozzle is charged with 540 g of a 16.7 mass % aqueous nitric acid solution and 230 g of methyl alcohol and air in the autoclave was replaced by nitrogen gas, and the inside of the autoclave was pressurized with nitrogen gas to a pressure of 0.4 MPa G. Then, a mixed gas of 10% by volume of nitrogen monoxide with nitrogen was fed into the autoclave at a feed rate of 16 N liter/hour through the gas feed nozzle while the reaction system is stirred, a portion of the gas fraction in the autoclave is withdrawn through the gas-withdrawing nozzle so that the pressure of the reaction system in the autoclave constant, and the temperature of the reaction system is increased to 50° C.

One hour after the stage at which the temperature of the reaction system reached 50° C., the composition of the gas fraction withdrawn at a flow rate of 19.2 N liter/hour from the autoclave was measured. As a result, the withdrawn gas fraction comprised 11.2% by volume of methyl nitrite, 2.1% by volume of nitrogen monoxide, 8.9% by volume of methyl alcohol, 2.8% by volume of water and 75% by volume of nitrogen. Further, 3 hours after the reaction temperature reached 50° C., the concentration of nitric acid in the liquid fraction contained in the autoclave was measured. As a result, the concentration of nitric acid was 9.5% by mass and thus the conversion rate of nitric acid was about 2 g/hour.

The results are shown in Table 1.

Examples 2 to 7

In each of Examples 2 to 7, the same procedures as in Example 1 were carried out except that the reaction temperature and pressure and the stirring conditions were changed as shown in Table 1, and in Example 7, the aqueous nitric acid solution was added with 0.2 mole/liter of a catalyst consisting of cupric nitrate. The results are shown in Table 1.

Comparative Example 1

The same procedures as in Example 1 were carried out, except that the aqueous nitric acid solution was replaced by 770 g of a 11.7 mass % aqueous nitric acid solution and no methyl alcohol was mixed into the aqueous nitric acid solution. One hour after the reaction temperature reached 50° C., the gas fraction withdrawn from the autoclave through the gas-withdrawing nozzle at a flow rate of 16.4 N liter/hr was subjected to an analysis. The gas fraction comprised 9.5% by volume of nitrogen monoxide, 0.5% by volume of nitrogen dioxide, 2.8% by volume of water and 8.72% by volume of nitrogen. No conversion of nitric acid during the reaction procedure was recognized.

TABLE 1

|  |  | Reaction conditions | | | Flow rate of mixed gas $(*)_1$ (N liter/hr) | MN concentration $(*)_2$ (% by volume) | Conversion rate of nitric acid (gHNO$_3$/hr) |
| --- | --- | --- | --- | --- | --- | --- | --- |
|  |  | Pressure (MPa G) | Temperature (° C.) | Stirring speed (rpm) | | | |
| Example | 1 | 0.4 | 50 | 1100 | 16 | 11.2 | 2 |
|  | 2 | 0.4 | 50 | 1100 | 60 | 10.5 | 6 |
|  | 3 | 0.4 | 27 | 1100 | 60 | 11.2 | 7 |
|  | 4 | 0.4 | 50 | 1100 | 180 | 9.7 | 16 |
|  | 5 | 0.4 | 50 | 2100 | 300 | 11.0 | 31 |
|  | 6 | 0.2 | 28 | 1100 | 16 | 6.0 | 1 |
|  | 7 | 0.2 | 28 | 1100 | 16 | 6.0 | 1 |

[Note]
$(*)_1$A mixed gas of 10% by volume of nitrogen monoxide with nitrogen
$(*)_2$Concentration of methyl nitrite in the withdrawn gas fraction Example 8

A reaction system as shown in FIG. 1 was employed. A reaction column 1 had an inside diameter of 158 mm and a height of 1400 mm and comprised an upper section 1a extending downward from a location of 50 mm below a top of the column at a length of 800 mm and packed with 100 mm Raschig rings and a lower section 1b extending downward from a location of 30 mm below the bottom end of the upper section 1a at a length of 400 mm and packed with 10 mm Raschig rings.

In to the reaction column 1, a material gas comprising 6.4% by volume of methyl nitrite, 12.6% by volume of nitrogen monoxide, 11.5% by volume of carbon monoxide, 4.8% by volume of methyl alcohol and 64.7% by volume of nitrogen was fed at a feed rate of 15.0 Nm$^3$/hr under a pressure of 0.32 MPa G (3.2 kg/cm$^2$ G) into an upper part of a bottom portion 1c through a pipe line 7; an oxygen gas was fed at a feed rate of 0.33 Nm$^3$/hr into the bottom portion 1c through a pipe lines 7a and 7; and methyl alcohol was fed at a temperature of 20° C. at a feed rate of 3.5 liters/hr into a top portion 1d of the reaction column 1 through a pipe line 4.

The pressure in the reaction column 1 was controlled to 0.3 MPa G (3.0 kg/cm$^2$ G) by using a valve placed in the pipe line 5.

A resultant liquid fraction (b) accumulated in the bottom portion 1c of the reaction column 1 was withdrawn through a pipe line 3. A major portion (b-2) of the withdrawn liquid fraction was introduced into a cooler 9 by using a pump (not shown in FIG. 1) placed in the pipe line 8 and cooled. The cooled portion (b-2) of the liquid fraction was returned at a flow rate of 360 liters/hr into the middle portion 1e of the reaction column. The cooler 9 was operated so that the temperature of the liquid fraction in the bottom portion 1c of the reaction column 1 can be adjusted to 40° C., by flowing a cooling water having a temperature of 5° C. through a cooling jacket (not shown in FIG. 1) of the cooler 9. After the reaction reached stable conditions, a gas fraction (a) comprising 14.72% by volume of methyl nitrite, 4.01% by volume of nitrogen monoxide, 11.54% by volume of carbon monoxide, 4.82% by volume of methyl alcohol, 64.92% by volume of nitrogen was delivered from the top portion 1d of the reaction column 1 through a pipe line 5 at a total flow rate of 14.95 Nm$^2$/hr.

Also, the liquid fraction comprised 57.4% by mass of methyl alcohol, 33.6% by mass of water, 8.6% by mass of nitric acid, and 0.5% by mass of methyl nitrite and was withdrawn at a flow rate of 1.75 liters/hr through the pipe line 3.

A 10 liter capacity autoclave reactor 2 made of SuS 316 was employed. The reactor 2 was equipped with two steps of disc turbines and a level meter and a stirrer, and connected to a pipe line 11 connected to a nitrogen monoxide supply source (not shown in FIG. 1), a pipe line 12 for discharging a liquid fraction (d) generated in the reactor 2 from the bottom portion 2c, the pipe line 3 through which a middle portion 2a of the reactor 2 is connected to the bottom of the reaction column 1, and a pipe line 10 through which the top portion 2b of the reactor 2 is connected to the pipe line 7 at a location upstream to the connection of the oxygen-feeding pipe line 7a and downstream from the connection of the nitrogen monoxide feeding pipe line 11 to the pipe line 7.

Into the reactor 2, a portion of the withdrawn liquid fraction from the reaction column 2 was fed in an amount of 6 liters through the pipe line 3, air in the inside of the reactor 2 was replaced by nitrogen gas, and the inside of the reactor 2 was pressurized with the nitrogen gas to a pressure of 0.3 MPa G (3 kg/cm$^2$ G). Then the nitrogen monoxide gas (the material gas) is introduced at a feed rate of 2 Nm$^3$/hr into the liquid fraction (b) in the reactor 2 through the pipe line 11, while the liquid fraction (b) in the reactor 2 was stirred at a stirring rate of 600 rpm, the temperature of the reaction system was increased to 50° C., and a resultant gas fraction is withdrawn through the pipe line 10 so that the pressure of the reaction system in the reactor 2 is maintained at the above-mentioned level. Simultaneously, a portion (b-1) of the withdrawn liquid fraction (b) from the reaction column 1 was introduced at a feed rate of 1.75 liters/hr into the reactor 2 through the pipe line 3. Also, a resultant liquid fraction (d) generated in the reactor 2 was withdrawn at a flow rate of 1.61 liters/hr through the pipe line 12 so that the reaction temperature was maintained constant at 50° C. and the liquid level of the reaction system is maintained constant at a liquid volume of about 0.8 liter.

The withdrawn liquid fraction (d) had a composition of 58.0% by mass of methyl alcohol, 37.4% by mass of water, 3.7% by mass of nitric acid and 0.4% by mass of methyl nitrite. In the reaction in the reactor 2, the conversion of nitric acid was 60.4% by mass. Also, the withdrawn gas fraction (c) had a composition of 9.42% by volume of methyl nitrite, 10.03% by volume of carbon dioxide, 11.36% by volume of carbon monoxide, 4.74% by volume of methyl alcohol and 63.93% by volume of nitrogen, and was introduced at a flow rate of 2 Nm$^3$/hr into the reaction column 1 through the pipe lines 10 and 7.

After the reaction conditions in the reaction column 1 and the reactor 2 became stable, the composition of the gas fraction (a) delivered from the reaction column 1 through the pipe line 5, was subjected to the gas analysis. It was confirmed that the gas fraction (a) comprised 15.56% by volume of methyl nitrite, 3.59% by volume of nitrogen monoxide, 11.50% by volume of carbon monoxide and 4.79% by volume of methyl alcohol and 64.56% by volume of nitrogen and was delivered at a total flow rate of 15.04 Nm$^3$/hr.

Example 9

The same reaction procedures as in Example 8 were carried out except that the reaction temperature in the autoclave reactor 2 was changed from 50° C. to 70° C.

After the temperature and liquid level in the autoclave reactor 2 became stable, the liquid fraction (d) was withdrawn from the reactor 2 at a flow rate of 1.61 liters/hr, had contents of methyl alcohol of 58.3% by mass, water of 39.2% by mass, nitric acid of 1.90% by mass and methyl nitrite of 0.4% by mass and exhibited a conversion of nitric acid of 79.6%.

Also, the gas fraction (c) was withdrawn from the reactor 2 and introduced at a flow rate of 2.1 Nm$^3$/hr into the reaction column 1 through the pipe lines 10 and 7. The withdrawn gas fraction comprised 11.15% by volume of methyl nitrite, 8.86% by volume of nitrogen monoxide, 10.98% by volume of carbon monoxide, 7.21% by volume of methyl alcohol and 61.79% by volume of nitrogen.

Further, after the reactions in the reaction column 1 and the autoclave reactor 2 became stable, the gas fraction (a) withdrawn from the top portion 1d of the reaction column 1 through the pipe line 5 was subjected to an analysis. It was confirmed that the gas fraction (a) comprised 15.69% by volume of methyl nitrite, 3.29% by volume of nitrogen monoxide, 11.39% by volume of carbon monoxide, 5.72% by volume of methyl alcohol and 63.92% by volume of nitrogen and was withdrawn at a total flow rate of 15.19 Nm$^3$/hr.

Comparative Example 2

The same reaction procedures as in Example 8 were carried out except that all the procedures relating to the autoclave reactor 2, including, for example, the introduction of the liquid fraction (b) from the reaction column 1 and the feed of the nitrogen monoxide gas and the reaction in the reactor 2, were omitted.

It was confirmed that the nitric acid produced as a by-product by the reaction in the reaction column 1 was not utilized to produce the target methyl nitrite, and thus the yield of the methyl nitrite could not be increased.

INDUSTRIAL APPLICABILITY

The process of the present invention enables an alkyl nitrite to be industrially produced with high efficiency, from nitric acid, nitrogen monoxide and an alkyl alcohol. In the process of the present invention, nitric acid produced as a by-product of a process for the production of an alkyl nitrite from an alkyl alcohol, nitrogen monoxide and oxygen can be utilized to enhance the yield of the target alkyl nitrite. Also, in the process of the present invention, an aqueous solution of nitric acid in a relatively low concentration and an alkyl alcohol can be used to produce the target alkyl nitrite with high efficiency.

The process of the present invention is very useful for a synthetic reaction using as material compounds, an alkyl nitrite ester and carbon monoxide, for example, a production of dialkyl oxalate ester or dialkyl carbonate ester. In this synthetic process, the process of the present invention contributes to decreasing the loss of nitrogen components such as nitric acid due to the discharge of the liquid fraction and as alkyl nitrite and nitrogen monoxide, due to the discharge of the gas fraction, generated by the reaction of an alkyl alcohol with nitrogen monoxide and oxygen, and saving the supplementation of the nitrogen components.

What is claimed is:

1. A process for producing an alkyl nitrite comprising bringing a nitrogen monoxide gas into contact with an aqueous solution of an alkyl alcohol and nitric acid, to produce an alkyl nitrite.

2. The process for producing an alkyl nitrite as claimed in claim 1, wherein the alkyl alcohol has 1 to 3 carbon atoms.

3. The process for producing an alkyl nitrite as claimed in claim 1, wherein the aqueous solution contains nitric acid in a concentration of 60% by mass or less.

4. The process for producing an alkyl nitrite as claimed in claim 1, wherein the aqueous solution contains the alkyl alcohol in a concentration of 5 to 70% by mass.

5. The process for producing an alkyl nitrite as claimed in claim 1, wherein the contact of the nitrogen monoxide gas with the aqueous solution of the alkyl alcohol and nitric acid is carried out at a temperature of from 0° C. to 200° C., under an ambient atmospheric pressure or more but not more than 20 MPa G.

6. The process for producing an alkyl nitrite as claimed in claim 1, wherein the aqueous solution of the alkyl alcohol and nitric acid further contains a catalyst comprises at least one nitrate salt of Group VIII metals except for platinum group metals and of Group IB metals of the Periodic Table.

7. The process for producing an alkyl nitrite as claimed in claim 6, wherein the catalyst is present in an amount, in terms of metal, of 20% by mass or less, based on the mass of the aqueous solution containing the alkyl alcohol and nitric acid.

8. The process for producing an alkyl nitrite as claimed in claim 1, wherein the nitrogen monoxide gas is substantially free from nitrogen oxides produced due to the presence of molecular oxygen in the nitrogen monoxide gas.

* * * * *